(12) United States Patent
Miller et al.

(10) Patent No.: US 7,871,967 B2
(45) Date of Patent: Jan. 18, 2011

(54) DIESTER-BASED LUBRICANTS AND METHODS OF MAKING SAME

(75) Inventors: Stephen Joseph Miller, San Francisco, CA (US); Saleh A. Elomari, Fairfield, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 854 days.

(21) Appl. No.: 11/673,879

(22) Filed: Feb. 12, 2007

(65) Prior Publication Data

US 2008/0194444 A1    Aug. 14, 2008

(51) Int. Cl.
*C10L 1/14*     (2006.01)
*C07C 55/02*    (2006.01)

(52) U.S. Cl. ........................ 508/459; 508/506
(58) Field of Classification Search ............... 508/459, 508/506
See application file for complete search history.

(56) References Cited

U.S. PATENT DOCUMENTS

| 5,629,440 | A | 5/1997 | Camenzind et al. |
| 5,798,054 | A | 8/1998 | Sato et al. |
| 6,165,952 | A | 12/2000 | Abramshe et al. |
| 6,703,353 | B1 | 3/2004 | Lok et al. |
| 2006/0019840 | A1* | 1/2006 | Kawahara et al. ........... 508/280 |

OTHER PUBLICATIONS

Dmytryshyn et al., "Synthesis and characterization of vegetable oil derived esters: evaluation for their diesel additive properties," Bioresource Technology 92 (2004) 55-64.

* cited by examiner

*Primary Examiner*—Walter D Griffin
*Assistant Examiner*—Frank C Campanell
(74) *Attorney, Agent, or Firm*—Edward T. Mickelson (57) ABSTRACT

The present invention is generally directed to diester-based lubricant compositions. The present invention is also directed to methods of making these and other similar lubricant compositions. In some embodiments, the methods for making such diester-based lubricants utilize a biomass precursor and/or low value Fischer-Tropsch (FT) olefins and/or alcohols so as to produce high value diester-based lubricants. In some embodiments, such diester-based lubricants are derived from FT olefins and fatty acids. The fatty acids can be from a bio-based source (i.e., biomass, renewable source) or can be derived from FT alcohols via oxidation.

16 Claims, 6 Drawing Sheets

Scheme 1

Fig. 1

Scheme 1

Hexanoic acid 1-ethyl-2-hexanoyloxy-butyl ester (3)

Octadecanoic acid 1-ethyl-2-octadecanoyloxy-butyl ester (4)

Fig. 4

Table 1

| Compound | VI | VIS cSt (40 °C) | VIS cSt (100 °C) | Pour point | Cloud Point |
|---|---|---|---|---|---|
|  Hexanoic acid 2-hexanoyloxy-1-hexyl-octyl ester (1) | 68 | 9.32 | 2.42 | <-60 | -50 |
|  Decanoic acid 2-decanoyloxy-1-hexyl-octyl ester (2) | 117 | 17.5 | 3.9 | -39 | 7 |
|  50/50 wt% mixture 50/50 mix of (1) and (2) | 101 | 12.8 | 3.1 | <-60 | -50 |

Fig. 5

Table 2

| Lubricant Composition | Oxidation Stability Hr/1L O$_2$ uptake |
|---|---|
| Group I Lubricants | 7.2 |
| Group III Lubricants | 41.2 |
| Cargill Agri-Pure 75, 85, 560 | 0.17, 0.3, 0.41 |
| 50/50 mix of (1) and (2) 50/50 wt% mixture | 11.49 |

Fig. 6

DIESTER-BASED LUBRICANTS AND METHODS OF MAKING SAME

FIELD OF THE INVENTION

This invention relates to ester-based lubricants, and specifically to diester-based lubricants, and methods of making them—particularly wherein they are made from at least one biologically-derived precursor and/or Fischer-Tropsch product(s).

BACKGROUND

Esters have been used as lubricating oils for over 50 years. They are used in a variety of applications ranging from jet engines to refrigeration. In fact, esters were the first synthetic crankcase motor oils in automotive applications. However, esters gave way to polyalphaolefins (PAOs) due to the lower cost of PAOs and their formulation similarities to mineral oils. In full synthetic motor oils, however, esters are almost always used in combination with PAOs to balance the effect on seals, additives solubility, volatility reduction, and energy efficiency improvement by enhanced lubricity.

Ester-based lubricants, in general, have excellent lubrication properties due to the polarity of the ester molecules of which they are comprised. The polar ester groups of such molecules adhere to positively-charged metal surfaces creating protective films which slow down the wear and tear of the metal surfaces. Such lubricants are less volatile than the traditional lubricants and tend to have much higher flash points and much lower vapor pressures. Ester lubricants are excellent solvents and dispersants, and can readily solvate and disperse the degradation by-products of oils. Therefore, they greatly reduce sludge buildup. While ester lubricants are stable to thermal and oxidative processes, the ester functionalities give microbes a handle to do their biodegrading more efficiently and more effectively than their mineral oil-based analogues. However, the preparation of esters is more involved and more costly than the preparation of their PAO counterparts.

In view of the foregoing, a simpler, more efficient method of generating ester-based lubricants would be extremely useful—particularly wherein such methods utilize renewable raw materials in combination with converting low value Fischer-Tropsch (FT) olefins and alcohols to high value ester lubricants.

BRIEF DESCRIPTION OF THE INVENTION

The present invention is generally directed to diester-based lubricant compositions. The present invention is also directed to methods of making these and other similar lubricant compositions. In some embodiments, the methods for making such diester-based lubricants utilize a biomass precursor. In these or other embodiments, lubricant precursor species can also be sourced or derived from Fischer-Tropsch (FT) reaction products.

In some embodiments, the present invention is directed to lubricant compositions comprising a quantity of at least one diester species, the diester species having the following structure:

wherein $R_1$, $R_2$, $R_3$, and $R_4$ are the same or independently selected from $C_2$ to $C_{17}$ hydrocarbon groups.

In some or other embodiments, the present invention is directed to processes comprising the steps of (a) epoxidizing an olefin having a carbon number of from 8 to 16 to form an epoxide comprising an epoxide ring; (b) opening the epoxide ring of the epoxide to form a diol; and (c) esterifying the diol with a $C_2$ to $C_{18}$ carboxylic acid to form a diester species having viscosity and pour point suitable for use as a lubricant.

In some or other embodiments, the present invention is directed to processes (i.e., methods) comprising the steps of: (a) epoxidizing an olefin having a carbon number of from 8 to 16 to form an epoxide comprising an epoxide ring; (b) opening the epoxide ring to form a diol; and (c) esterifying the diol with a $C_2$ to $C_{18}$ carboxylic acids or their acylating derivatives such as acyl chloride or anhydrides to form a diester species having viscosity and pour point suitable for use as a lubricant.

In some or still other embodiments, the present invention is directed to processes comprising the steps of: (a) epoxidizing a plurality of olefins, the olefins having a carbon number of from 8 to 16, to form a plurality of epoxides; (b) converting the epoxides to diols; and (c) esterifying the diols with a $C_2$ to $C_{18}$ esterifying species to form a plurality of diesters having viscosity and pour point suitable for use as a lubricant.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

1. Introduction

The present invention is directed to diester-based lubricant compositions. The present invention is also directed to methods of making these and other similar lubricant compositions. In some embodiments, the methods for making such diester-based lubricants utilize a biomass precursor and/or low value Fischer-Tropsch (FT) olefins and/or alcohols so as to produce high value diester-based lubricants. In some embodiments, such diester-based lubricants are derived from FT olefins and fatty (carboxylic) acids. In these or other embodiments, the fatty acids can be from a bio-based source (i.e., biomass, renewable source) or can be derived from FT alcohols via oxidation.

Because biolubricants and biofuels are increasingly gaining ground and becoming topics of focus for many in the oil industry, the use of biomass in the making of such above-mentioned lubricants could be attractive from several different perspectives. To the extent that biomass is so utilized in making the diester-based lubricants of the present invention, such lubricants are deemed to be biolubricants.

2. Definitions

"Lubricants," as defined herein, are substances (usually a fluid under operating conditions) introduced between two moving surfaces so to reduce the friction and wear between them. Base oils used as motor oils are generally classified by the American Petroleum Institute as being mineral oils (Group I, II, and III) or synthetic oils (Group IV and V). See American Petroleum Institute (API) Publication Number 1509.

"Pour point," as defined herein, represents the lowest temperature at which a fluid will pour or flow. See, e.g., ASTM International Standard Test Methods D 5950-96, D 6892-03, and D 97.

"Cloud point," as defined herein, represents the temperature at which a fluid begins to phase separate due to crystal formation. See, e.g., ASTM Standard Test Methods D 5773-95, D 2500, D 5551, and D 5771.

"Centistoke," abbreviated "cSt," is a unit for kinematic viscosity of a fluid (e.g., a lubricant), wherein 1 centistoke equals 1 millimeter squared per second (1 cSt=1 mm$^2$/s). See, e.g., ASTM Standard Guide and Test Methods D 2270-04, D 445-06, D 6074, and D 2983.

With respect to describing molecules and/or molecular fragments herein, "$R_n$," where "n" is an index, refers to a hydrocarbon group, wherein the molecules and/or molecular fragments can be linear and/or branched.

As defined herein, "$C_n$," where "n" is an integer, describes a hydrocarbon molecule or fragment (e.g., an alkyl group) wherein "n" denotes the number of carbon atoms in the fragment or molecule.

The prefix "bio," as used herein, refers to an association with a renewable resource of biological origin, such as resource generally being exclusive of fossil fuels.

The term "internal olefin," as used herein, refers to an olefin (i.e., an alkene) having a non-terminal carbon-carbon double bond (C=C). This is in contrast to "α-olefins" which do bear a terminal carbon-carbon double bond.

3. Diester Lubricant Compositions

In some embodiments, the present invention is generally directed to diester-based lubricant compositions comprising a quantity of diester species having the following chemical structure:

where $R_1$, $R_2$, $R_3$, and $R_4$ are the same or independently selected from a $C_2$ to $C_{17}$ carbon fragment.

Regarding the above-mentioned diester species, selection of $R_1$, $R_2$, $R_3$, and $R_4$ can follow any or all of several criteria. For example, in some embodiments, $R_1$, $R_2$, $R_3$, and $R_4$ are selected such that the kinematic viscosity of the composition at a temperature of 100° C. is typically 3 centistokes (cSt) or greater. In some or other embodiments, $R_1$, $R_2$, $R_3$, and $R_4$ are selected such that the pour point of the resulting lubricant is −20° C. or lower. In some embodiments, $R_1$ and $R_2$ are selected to have a combined carbon number (i.e., total number of carbon atoms) of from 6 to 14. In these or other embodiments, $R_3$ and $R_4$ are selected to have a combined carbon number of from 10 to 34. Depending on the embodiment, such resulting diester species can have a molecular mass between 340 atomic mass units (a.m.u.) and 780 a.m.u.

In some embodiments, such above-described compositions are substantially homogeneous in terms of their diester component. In some or other embodiments, the diester component of such compositions comprises a variety (i.e., a mixture) of diester species.

In some embodiments, the diester-based lubricant composition comprises at least one diester species derived from a $C_8$ to $C_{14}$ olefin and a $C_6$ to $C_{14}$ carboxylic acid. Typically, the diester species are made by reacting each —OH group (on the intermediate) with a different acid, but such diester species can also be made by reacting each —OH group with the same acid.

In some of the above-described embodiments, the diester-based lubricant composition comprises a diester species selected from the group consisting of decanoic acid 2-decanoyloxy-1-hexyl-octyl ester and its isomers, tetradecanoic acid-1-hexyl-2-tetradecanoyloxy-octyl esters and its isomers, dodecanoic acid 2-dodecanoyloxy-1-hexyl-octyl ester and its isomers, hexanoic acid 2-hexanoyloxy-1-hexy-octyl ester and its isomers, octanoic acid 2-octanoyloxy-1-hexyl-octyl ester and its isomers, hexanoic acid 2-hexanoyloxy-1-pentyl-heptyl ester and isomers, octanoic acid 2-octanoyloxy-1-pentyl-heptyl ester and isomers, decanoic acid 2-decanoyloxy-1-pentyl-heptyl ester and isomers, decanoic acid-2-cecanoyloxy-1-pentyl-heptyl ester and its isomers, dodecanoic acid-2-dodecanoyloxy-1-pentyl-heptyl ester and isomers, tetradecanoic acid 1-pentyl-2-tetradecanoyloxy-heptyl ester and isomers, tetradecanoic acid 1-butyl-2-tetradecanoyloxy-hexy ester and isomers, dodecanoic acid-1-butyl-2-dodecanoyloxy-hexyl ester and isomers, decanoic acid 1-butyl-2-decanoyloxy-hexyl ester and isomers, octanoic acid 1-butyl-2-octanoyloxy-hexyl ester and isomers, hexanoic acid 1-butyl-2-hexanoyloxy-hexyl ester and isomers, tetradecanoic acid 1-propyl-2-tetradecanoyloxy-pentyl ester and isomers, dodecanoic acid 2-dodecanoyloxy-1-propyl-pentyl ester and isomers, decanoic acid 2-decanoyloxy-1-propyl-pentyl ester and isomers, octanoic acid 1-2-octanoyloxy-1-propyl-pentyl ester and isomers, hexanoic acid 2-hexanoyloxy-1-propyl-pentyl ester and isomers, and mixtures thereof.

In some embodiments, the diester-based lubricant composition further comprises a base oil selected from the group consisting of Group I oils, Group II oils, Group III oils, and mixtures thereof.

It is worth noting that in most applications, the above-described esters and their compositions are unlikely to be used as lubricants by themselves, but are usually used as blending stocks. As such, esters with higher pour points may also be used as blending stocks with other lubricant oils since they are very soluble in hydrocarbons and hydrocarbon-based oils.

4. Methods of Making Diester Lubricants

As mentioned above, the present invention is additionally directed to methods of making the above-described lubricant compositions.

Figure 1:
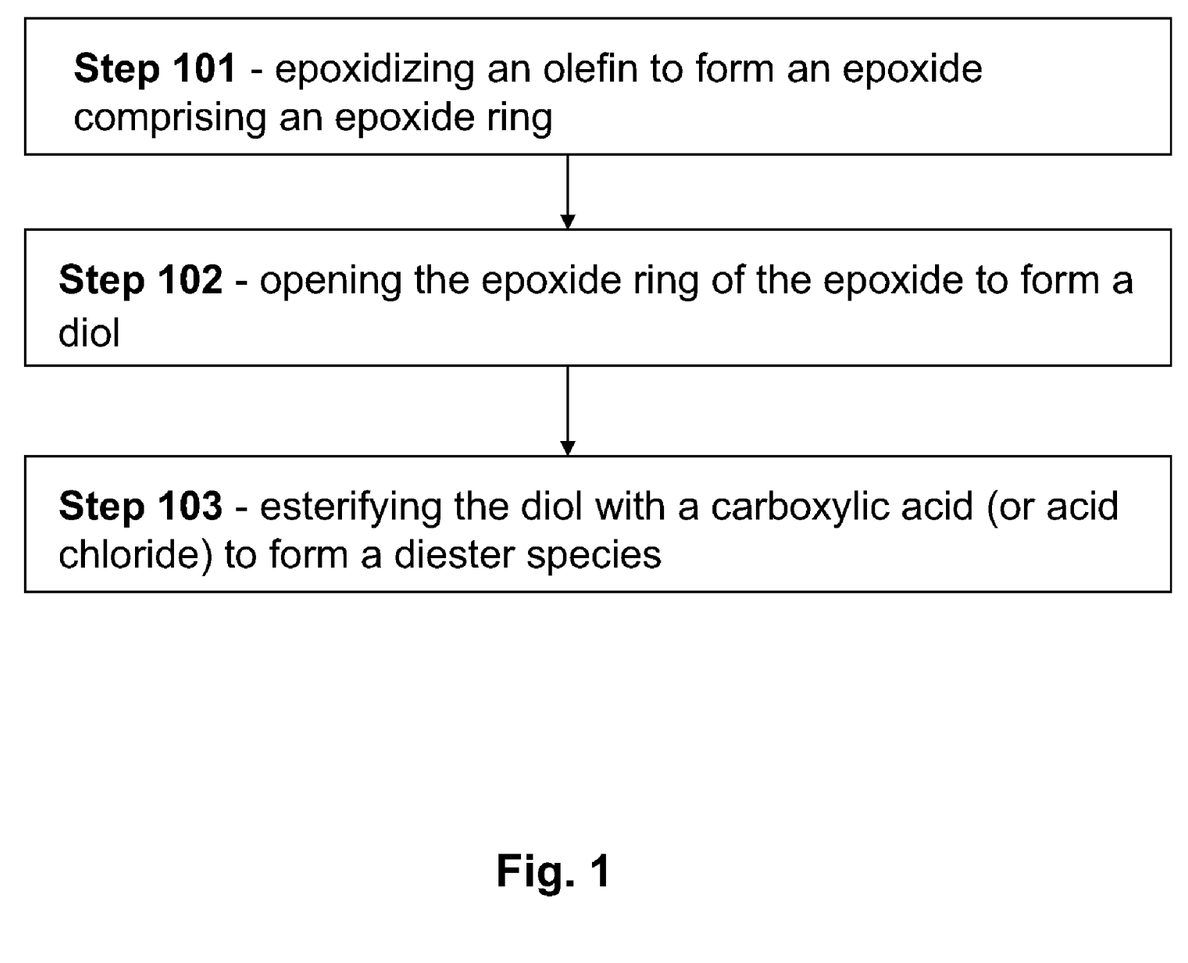
FIG. 1 is a flow diagram illustrating a method of making diester-based lubricant compositions, in accordance with some embodiments of the present invention.

Referring to the flow diagram shown in FIG. 1, in some embodiments, processes for making the above-mentioned diester species, typically having lubricating base oil viscosity and pour point, comprise the following steps: (Step 101) epoxidizing an olefin (or quantity of olefins) having a carbon number of from 8 to 16 to form an epoxide comprising an epoxide ring; (Step 102) opening the epoxide ring to form a diol; and (Step 103) esterifying (i.e., subjecting to esterification) the diol with a $C_2$ to $C_{18}$ carboxylic acid to form a diester species. Generally, lubricant compositions comprising such diester species have a viscosity of 3 centistokes or more at a temperature of 100° C.

In some embodiments, where a quantity of such diester species is formed, the quantity of diester species can be substantially homogeneous, or it can be a mixture of two or more different such diester species.

In some such above-described method embodiments, the olefin used is a reaction product of a Fischer-Tropsch process. In these or other embodiments, the carboxylic acid can be derived from alcohols generated by a Fischer-Tropsch process and/or it can be a bio-derived fatty acid.

In some embodiments, the olefin is an α-olefin (i.e., an olefin having a double bond at a chain terminus). In such embodiments, it is usually necessary to isomerize the olefin so as to internalize the double bond. Such isomerization is typically carried out catalytically using a catalyst such as, but not limited to, crystalline aluminosilicate and like materials and aluminophosphates. See, e.g., U.S. Pat. Nos. 2,537,283; 3,211,801; 3,270,085; 3,327,014; 3,304,343; 3,448,164; 4,593,146; 3,723,564 and 6,281,404; the last of which claims a crystalline aluminophosphate-based catalyst with 1-dimensional pores of size between 3.8 Å and 5 Å.

Figure 2:
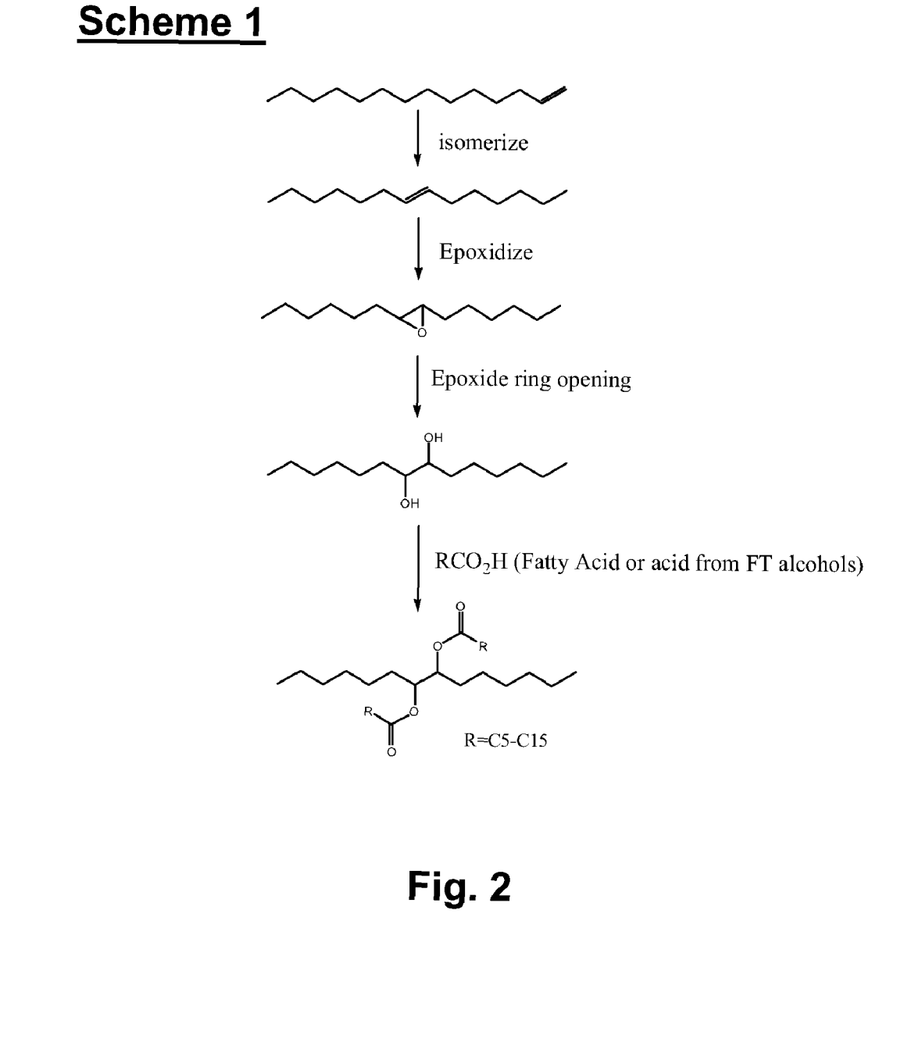
FIG. 2 (Scheme 1) is a chemical flow diagram illustrating an exemplary method of making a diester-based lubricant composition, in accordance with some embodiments of the present invention.

As an example of such above-described isomerizing and as indicated in Scheme 1 (FIG. 2), Fischer-Tropsch alpha olefins (α-olefins) can be isomerized to the corresponding internal olefins followed by epoxidation. The epoxides can then be transformed to the corresponding diols via epoxide ring opening followed by di-acylation (i.e., di-esterification) with the appropriate carboxylic acids or their acylating derivatives. It is typically necessary to convert alpha olefins to internal olefins because diesters of alpha olefins, especially short chain alpha olefins, tend to be solids or waxes. "Internalizing" alpha olefins followed by transformation to the diester functionalities introduces branching along the chain which reduces the pour point of the intended products. The ester groups with their polar character would further enhance the viscosity of the final product. Adding branches during the isomerizing (isomerization) step will tend to increase carbon number and hence viscosity. It can also decrease the associated pour and cloud points. It is typically preferable to have a few longer branches than many short branches, since increased branching tends to lower the viscosity index (VI).

Regarding the step of epoxidizing (i.e., the epoxidation step), in some embodiments, the above-described olefin (preferably an internal olefin) can be reacted with a peroxide (e.g., $H_2O_2$) or a peroxy acid (e.g., peroxyacetic acid) to generate an epoxide. See, e.g., D. Swern, in *Organic Peroxides Vol. II*, Wiley-Interscience, New York, 1971, pp. 355-533; and B. Plesnicar, in Oxidation in *Organic Chemistry, Part C*, W. Trahanovsky (ed.), Academic Press, New York 1978, pp. 221-253. Olefins can be efficiently transformed to the corresponding diols by highly selective reagent such as osmium tetra-oxide (M. Schroder, Chem. Rev. vol. 80, p. 187, 1980) and potassium permanganate (Sheldon and Kochi, in *Metal-Catalyzed Oxidation of Organic Compounds*, pp. 162-171 and 294-296, Academic Press, New York, 1981).

Regarding the step of epoxide ring opening to the corresponding diol, this step can be acid-catalyzed or based-catalyzed hydrolysis. Exemplary acid catalysts include, but are not limited to, mineral-based Brönsted acids (e.g., HCl, $H_2SO_4$, $H_3PO_4$, perhalogenates, etc.), Lewis acids (e.g., $TiCl_4$ and $AlCl_3$) solid acids such as acidic aluminas and silicas or their mixtures, and the like. See, e.g., Chem. Rev. vol. 59, p. 737, 1959; and Angew. Chem. Int. Ed., vol. 31, p. 1179, 1992. Based-catalyzed hydrolysis typically involves the use of bases such as aqueous solutions of sodium or potassium hydroxide.

Regarding the step of esterifying (esterification), an acid is typically used to catalyze the reaction between the —OH groups of the diol and the carboxylic acid(s). Suitable acids include, but are not limited to, sulfuric acid (Munch-Peterson, Org. Synth., V, p. 762, 1973), sulfonic acid (Allen and Sprangler, Org Synth., III, p. 203, 1955), hydrochloric acid (Eliel et al., Org Synth., IV, p. 169, 1963), and phosphoric acid (among others). In some embodiments, the carboxylic acid used in this step is first converted to an acyl chloride (via, e.g., thionyl chloride or $PCl_3$). Alternatively, an acyl chloride could be employed directly. Wherein an acyl chloride is used, an acid catalyst is not needed and a base such as pyridine, 4-dimethylaminopyridine (DMAP) or triethylamine (TEA) is typically added to react with an HCl produced. When pyridine or DMAP is used, it is believed that these amines also act as a catalyst by forming a more reactive acylating intermediate. See, e.g., Fersh et al., J. Am. Chem. Soc., vol. 92, pp. 5432-5442, 1970; and Hofle et al., Angew. Chem. Int. Ed. Engl., vol. 17, p. 569, 1978.

Regardless of the source of the olefin, in some embodiments, the carboxylic acid used in the above-described method is derived from biomass. In some such embodiments, this involves the extraction of some oil (e.g., triglyceride) component from the biomass and hydrolysis of the triglycerides of which the oil component is comprised so as to form free carboxylic acids.

Figure 3:
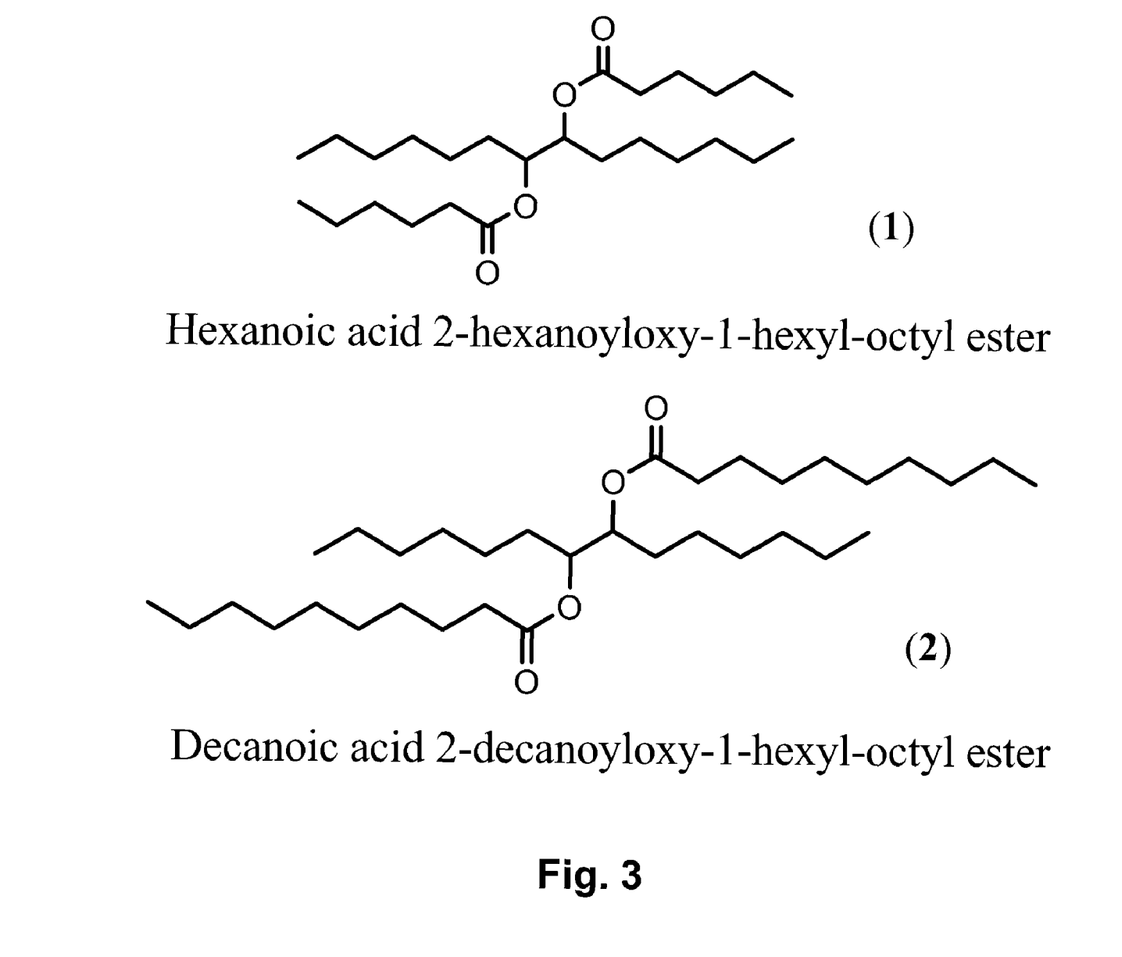
FIG. 3 depicts two exemplary diester-based compounds 1 and 2, suitable for use as lubricants in accordance with some embodiments of the present invention.

Using a synthetic strategy in accordance with that outlined in Scheme 1 (FIG. 2), 7-tetradecene was converted to diester derivatives 1 and 2 via acylation of tetradecane-7,8-diol intermediate with hexanoyl and decanoyl chlorides, respectively, as shown in FIG. 3.

5. Variations

Variations (i.e., alternate embodiments) on the above-described lubricant compositions include, but are not limited to, utilizing mixtures of isomeric olefins and or mixtures of olefins having a different number of carbons. This leads to diester mixtures in the product compositions.

Variations on the above-described processes include, but are not limited to, using carboxylic acids derived from FT alcohols by oxidation.

6. Examples

The following examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

As an exemplary synthetic procedure, the synthesis of a diester derived from 7-tetradecene and decanoyl chloride is described in Examples 1-2. This procedure is representative for making diesters from internal olefins and carboxylic acid chlorides (acyl chlorides), in accordance with some embodiments of the present invention.

EXAMPLE 1

This Example serves to illustrate synthesis of a diol en route to synthesis of a diester species, in accordance with some embodiments of the present invention.

In a 3-neck 1 mL reaction flask equipped with an overhead stirrer and an ice bath, 75 mL of 30% hydrogen peroxide were added to 300 mL of 96% formic acid. To this mixture, 100 g (0.51 mole) of 7-tetradecene (purchased from Aldrich Chemical Co.) was added slowly over a 30 minute period via a dropping funnel. Once the addition of the olefin was complete, the reaction was allowed to stir while cooling with the ice-bath to prevent rise in the temperature above 40-50° C. for 2 hrs. The ice-bath was then removed and the reaction was stirred at room temperature overnight. The reaction mixture was concentrated with a rotary evaporator in a hot water bath at ~30 torr to remove most of the water and formic acid. Then, 100 mL of ice-cold 1 M solution of sodium hydroxide was added very slowly (in small portions) and carefully to the remaining residue of the reaction. Once all the sodium hydroxide solution was added, the mixture was allowed to stir for an additional 45-60 minutes at room temperature. The mixture was diluted with 500 mL ethyl acetate and transferred to a separatory funnel. The organic layer was sequestered and the aqueous layer was extracted 3 times (3×200 mL) with ethyl acetate. The ethyl acetate extracts were combined and dried over anhydrous $MgSO_4$. Filtration, followed by concentration on a rotary evaporator at reduced pressure in a hot water bath gave the desired diol as white powder in 88% yield (95 g). The diol (tetradecane-7,8-diol) was characterized by nuclear magnetic resonance (NMR) spectroscopy and gas-chromatography/mass spectrometry (GC/MS).

EXAMPLE 2

This Example serves to illustrate synthesis of diester 2 (decanoic acid 2-decanoyloxy-1-hexyl-octyl ester) from tetradecane-7,8-diol.

In a 3-neck 1 L reaction flask equipped with an overhead stirrer, reflux condenser and a dropping funnel, 50 g (0.23 mol) of tetradecane-7,8-diol (see Example 1) and 60 g (0.59 mol) triethylamine and a catalytic amount of dimethylaminopyridine (6.5 gm; 0.052 mol)) were mixed in 500 mL anhydrous hexane. The solution was cooled down with an ice bath. To this solution 97 g (0.51 mol) decanoyl chloride was added drop-wise over a 15 minute period. Once the addition was complete, the ice bath was removed and the reaction was allowed to stir overnight. Then, an additional 12 g of the decanoyl chloride was added and the reaction was refluxed overnight. The resulting "milky" reaction solution was then neutralized with water. The resulting two layer mixture was then transferred to a separatory funnel. The organic (top) layer was separated and washed with 2×500 mL water. The aqueous layer was extracted with 3×300 mL ether. The ether extracts and the original organic layer were combined, dried over $MgSO_4$, filtered, and concentrated over a rotary evaporator at reduced pressure. The resulting residue was analyzed by NMR and infrared (IR) spectroscopies and GC/MS. Such analysis confirmed the presence of decanoic acid. The mixture was treated with 3 M aqueous solution of sodium carbonate (to neutralize the acid impurity) in 500 mL hexane. The hexane layer was dried over $MgSO_4$, filtered and concentrated on a rotary evaporator to give the desired diester product as a colorless viscous oil with a sweet odor in 81% yield (100.5 g). GC/MS indicated the presence of less than 1% residual acid in the product.

EXAMPLE 3

Using the procedure described above for making diester 2, diester 1 was prepared from 7-tetradecene and hexanoyl chloride. Diester 1 was obtained as colorless oil with a pleasant odor in 74% overall yield (starting form the 7-tetradecene).

COMPARATIVE EXAMPLE 4

This Example serves to illustrate the effect a high level of symmetry may have on the lubricant properties of the final diester product.

Figure 4:
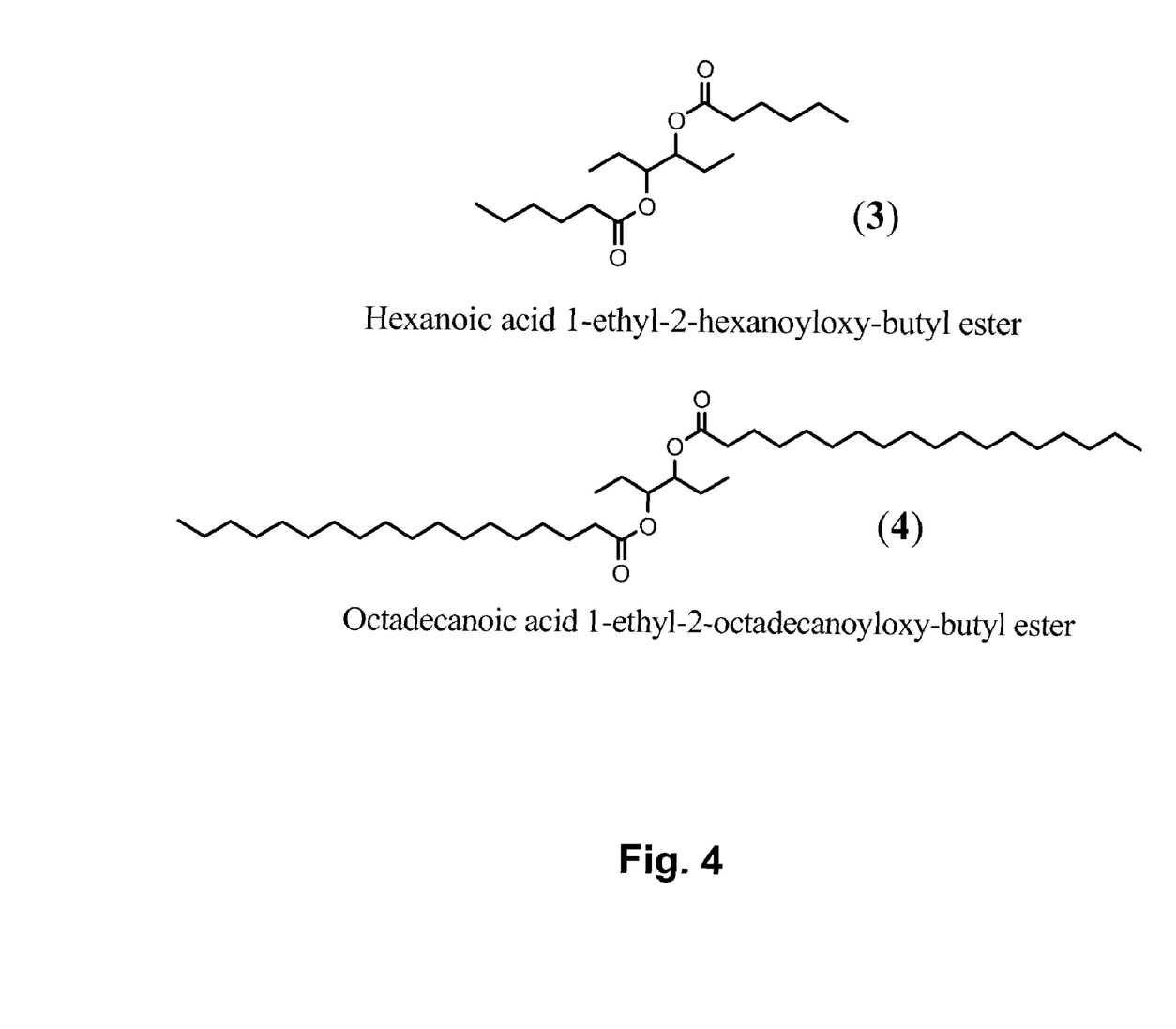
FIG. 4 depicts two diester-based compounds 3 and 4, made in accordance with some embodiments of the present invention.

Two diester derivatives of 3-hexene (3 and 4, depicted in FIG. 4) were not oils—they both were solid (waxy) materials. This may have to do with the very high symmetry of these molecules leading to better "packability" of the molecules and resulting in solid products. Diesters 1 and 2 are also symmetrical, but the longer backbone of 7-tetradecene may "twist" and "wiggle" enough to prevent them from having the ability to pack well and form solids. In contrast to diesters 3 and 4, diester species used in accordance with the present invention tend to be selected so as to avoid such enhanced packability.

EXAMPLE 5

This Example serves to illustrate the lubrication properties of some exemplary bioesters suitable for use as lubricants, in accordance with some embodiments of the present invention.

Figure 5:
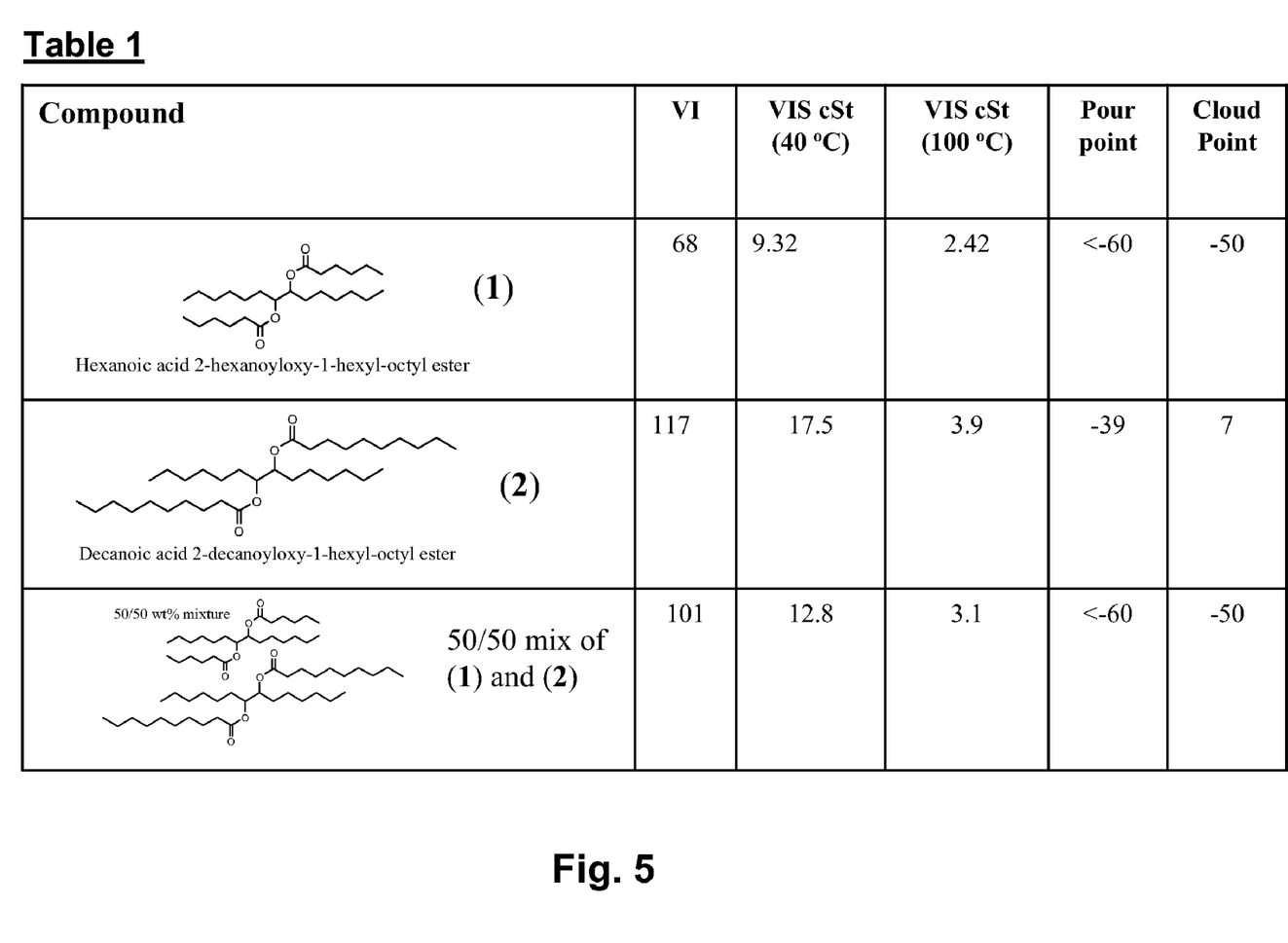
FIG. 5 (Table 1) compares lubrication properties of diester-based lubricants 1 and 2 and their mixture.

Esters 1 and 2 were prepared as described above and were tested and analyzed for several physical and lubricant properties including viscosity, viscosity index, cloud point, pour point and oxidation stability (see, e.g., ASTM Standard Test Method D 4636). These esters showed very promising lubricant properties. Table 1 (FIG. 5) summarizes the results of some of these tests and analyses.

EXAMPLE 6

Figure 6:
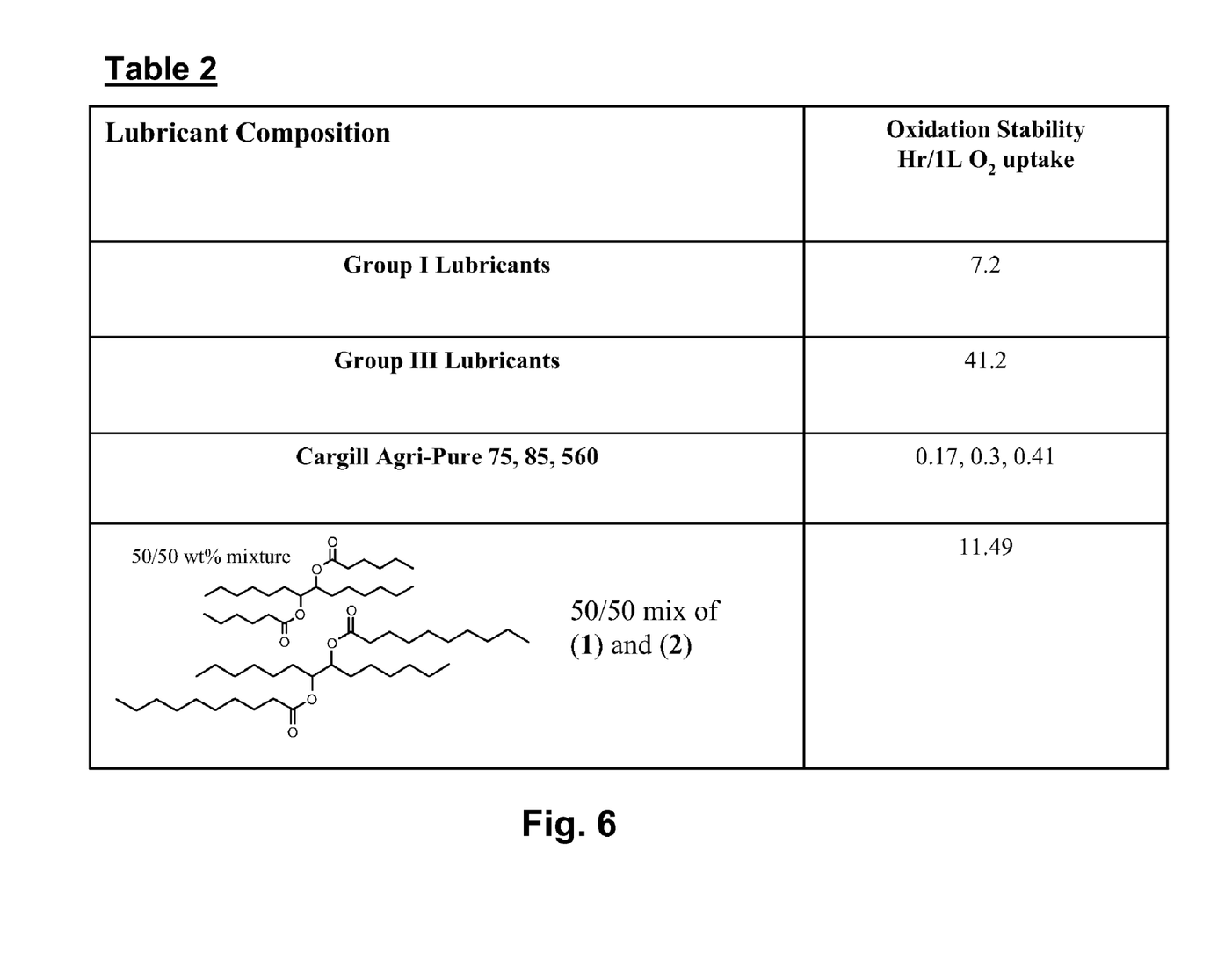
FIG. 6 (Table 2) compares oxidation stability of representative diester-based lubricants to that of other commercially-available lubricants.

This Example serves to illustrate the oxidation stability of some diester-based lubricant compositions and their comparison with other lubricant products. The associated data is shown in Table 2 (FIG. 6).

Referring to Table 2, the oxidation results for diesters 1 and 2 appear to resemble those of Group I oils. However, the oxidation stability of these diesters is superior to those of commercially-available bioesters. The Cargill Agri-Pure biolubricants 75 and 85 are high oleic canola oils, while Agri-Pure 560 is a synthetic polyol ester. In comparison to currently-available biolubricants, such diester compositions (e.g., 1 and 2) fare very well on all fronts: viscosity index (VI), viscosity (Vis), pour point, cloud point and oxidation stability. In fact, such diester compositions of the present invention are superior in their oxidation stabilities to the current market biolubes.

7. Summary

In summary, the present invention provides for diester-based lubricant compositions. The present invention also provides for methods (processes) of making these and other similar lubricant compositions. In some embodiments, the methods for making such diester-based lubricants utilize a biomass precursor and/or low value Fischer-Tropsch olefins and/or alcohols so as to produce high value diester-based lubricants. In some embodiments, such diester-based lubricants are derived from FT olefins and fatty acids. The fatty acids can be from a bio-based source (i.e., biomass, renewable source) or can be derived from FT alcohols via oxidation.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A lubricant composition comprising a quantity of at least one diester species, the diester species having the following structure:

wherein $R_1$, $R_2$, $R_3$, and $R_4$ are the same or independently selected from $C_2$ to $C_{17}$ hydrocarbon groups.

2. The lubricant composition of claim 1, wherein the kinematic viscosity of the composition at a temperature of 100° C. is 3 centistokes or greater.

3. The lubricant composition of claim 1, wherein the pour point is −20° C. or lower.

4. The lubricant composition of claim 1, wherein $R_1$ and $R_2$ are selected to have a combined carbon number of from at least about 6 to at most about 14.

5. The lubricant composition of claim 1, wherein $R_3$ and $R_4$ are selected to have a combined carbon number of from at least about 10 to at most about 34.

6. The lubricant composition of claim 1, wherein said composition comprises quantities of at least two different diester species.

7. The lubricant composition of claim 1, wherein the at least one diester species has a molecular mass that is from at least about 340 a.m.u. to at most about 780 a.m.u.

8. The lubricant composition of claim 1, wherein the at least one diester species is selected from the group consisting of decanoic acid 2-decanoyloxy-1-hexyl-octyl ester, tetradecanoic acid-1-hexyl-2-tetradecanoyloxy-octyl esters, dodecanoic acid 2-dodecanoyloxy-1-hexyl-octyl ester, hexanoic acid 2-hexanoyloxy-1-hexy-octyl ester, octanoic acid 2-octanoyloxy-1-hexyl-octyl ester hexanoic acid 2-hexanoyloxy-1-pentyl-heptyl ester, octanoic acid 2-octanoyloxy-1-pentyl-heptyl ester, decanoic acid 2-decanoyloxy-1-pentyl-heptyl ester, decanoic acid-2-decanoyloxy-1-pentyl-heptyl ester, dodecanoic acid-2-dodecanoyloxy-1-pentyl-heptyl ester, tetradecanoic acid 1-pentyl-2-tetradecanoyloxy-heptyl ester, tetradecanoic acid 1-butyl-2-tetradecanoyloxy-hexy ester, dodecanoic acid-1-butyl-2-dodecanoyloxy-hexyl ester, decanoic acid 1-butyl-2-decanoyloxy-hexyl ester, octanoic acid 1-butyl-2-octanoyloxy-hexyl ester, hexanoic acid 1-butyl-2-hexanoyloxy-hexyl ester, tetradecanoic acid 1-propyl-2-tetradecanoyloxy-pentyl ester, dodecanoic acid 2-dodecanoyloxy-1-propyl-pentyl ester, decanoic acid 2-decanoyloxy-1-propyl-pentyl ester, octanoic acid 1- 2-octanoyloxy-1-propyl-pentyl ester, hexanoic acid 2-hexanoyloxy-1-propyl-pentyl ester, and mixtures thereof.

9. The lubricant composition of claim 1, further comprising a base oil selected from the group consisting of Group I oils, Group II oils, Group III oils, and mixtures thereof.

10. A lubricant composition comprising a quantity of at least one diester species, the diester species having the following structure:

wherein $R_1$ and $R_2$, are the same or independently selected from $C_5$ to $C_{17}$ hydrocarbon groups, wherein $R_3$, and $R_4$ are the same or independently selected from $C_2$ to $C_{17}$ hydrocarbon groups, wherein the kinematic viscosity of the composition at a temperature of 100° C. is 3 centistokes or greater, and wherein the pour point is −20° C. or lower.

11. The lubricant composition of claim 10, wherein $R_3$ and $R_4$ are selected to have a combined carbon number of from at least about 10 to at most about 34.

12. The lubricant composition of claim 10, wherein said composition comprises quantities of at least two different diester species.

13. The lubricant composition of claim 10, wherein the at least one diester species has a molecular mass that is from at least about 340 a.m.u. to at most about 780 a.m.u.

14. The lubricant composition of claim 10, further comprising a base oil selected from the group consisting of Group I oils, Group II oils, Group III oils, and mixtures thereof.

15. A lubricant composition comprising a quantity of at least one diester species, the diester species having the following structure:

wherein $R_1$ and $R_2$, are selected to have a combined carbon number of from at least about 10 to at most about 14, wherein $R_3$, and $R_4$ are selected to have a combined carbon number of from at least about 12 to at most about 28, wherein the kinematic viscosity of the composition at a temperature of 100° C. is 3 centistokes or greater, and wherein the pour point is −20° C. or lower.

16. The lubricant composition of claim 15, further comprising a base oil selected from the group consisting of Group I oils, Group II oils, Group III oils, and mixtures thereof.

* * * * *